United States Patent [19]

Engel et al.

[11] Patent Number: 4,536,402
[45] Date of Patent: Aug. 20, 1985

[54] VINYLOGOUS CARBOXAMIDES

[75] Inventors: Wolfhard Engel; Eckhart Bauer, both of Biberach; Günter Trummlitz, Warthausen; Peter Danneberg, Ockenheim; Joachim Kähling, Biberach, all of Fed. Rep. of Germany

[73] Assignee: Dr. Karl Thomae Gesellschaft mit beschränkter Haftung, Biberach, Fed. Rep. of Germany

[21] Appl. No.: 676,067

[22] Filed: Nov. 29, 1984

Related U.S. Application Data

[63] Continuation-in-part of Ser. No. 478,673, Mar. 25, 1983.

Foreign Application Priority Data

Apr. 6, 1982 [DE] Fed. Rep. of Germany ....... 3212752

[51] Int. Cl.³ .................... A61K 31/44; A61K 31/38; C07D 333/52
[52] U.S. Cl. .................... 514/443; 549/53; 546/274; 514/337
[58] Field of Search .................... 549/53; 546/274; 424/263, 275

[56] References Cited

U.S. PATENT DOCUMENTS 3,070,606 12/1962 Anderson .............................. 549/49
4,288,437 9/1981 Engel et al. ......................... 424/246

Primary Examiner—Alan Siegel
Attorney, Agent, or Firm—Hammond & Littell, Weissenberger & Dippert

[57] ABSTRACT

Compounds of the formula

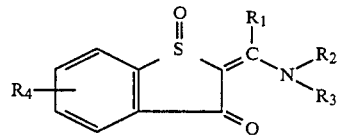

wherein
$R_1$ is phenyl, halo- and/or methyl-substituted phenyl or pyridinyl;
$R_2$ is hydrogen, straight or branched alkyl of 1 to 4 carbon atoms, 2- or 3-hydroxy-(alkyl of 2 to 3 carbon atoms) or 2- or 3-dimethylamino-(alkyl of 2 to 3 carbon atoms);
$R_3$ is hydrogen or alkyl of 1 to 3 carbon atoms; and
$R_4$ is hydrogen, chlorine or methyl.

The compounds are useful as anticonvulsants.

8 Claims, No Drawings

VINYLOGOUS CARBOXAMIDES

This is a continuation-in-part of copending application Ser. No. 478,673, filed Mar. 25, 1983.

This invention relates to novel vinylogous carboxamides, to methods of preparing these compounds, to pharmaceutical compositions containing them as active ingredients, and to a method of using them as anticonvulsants.

More particularly, the present invention relates to a novel class of vinylogous carboxamides represented by the formula

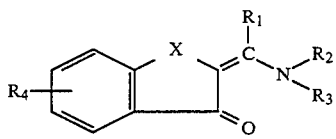

wherein
X is sulfinyl;
$R_1$ is phenyl, halo-substituted phenyl, methyl-substituted phenyl, halo- and methyl-substituted phenyl or pyridinyl;
$R_2$ is hydrogen, straight or branched alkyl of 1 to 4 carbon atoms, 2- or 3-hydroxy-(alkyl of 2 to 3 carbon atoms) or 2- or 3-dimethylamino-(alkyl of 2 to 3 carbon atoms);
$R_3$ is hydrogen or alkyl of 1 to 3 carbon atoms; and
$R_4$ is hydrogen, chlorine or methyl.

A preferred subgenus is constituted by those compounds of the formula I wherein
X is sulfinyl;
$R_1$ is phenyl, methyl-phenyl, fluoro-phenyl, chloro-phenyl or bromo-phenyl;
$R_2$ is hydrogen, alkyl of 1 to 3 carbon atoms or 2-hydroxy-ethyl;
$R_3$ is hydrogen or methyl; and
$R_4$ is hydrogen, chlorine or methyl.

An especially preferred subgenus is constituted by those compounds of the formula I, wherein
X is sulfinyl,
$R_1$ is phenyl, 2-methyl-phenyl, 2-chloro-phenyl or 2-bromo-phenyl, and
$R_2$, $R_3$ and $R_4$ are each hydrogen.

Those compounds embraced by formula I may be prepared by oxidizing a compound of the formula

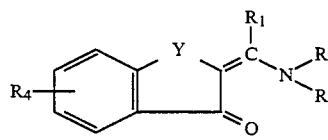

wherein
$R_1$, $R_2$, $R_3$ and $R_4$ have the meanings previously defined, and
Y is sulfur.

The oxidation is preferably carried out in a solvent or mixture of solvents, such as water, pyridine, methanol, ethanol, acetone, acetic acid, formic acid, trifluoroacetic acid, dichloromethane, trichloromethane or mixtures of any two or more of these, depending on the particular oxidizing agent which is used, and at temperatures between −80° C. and 120° C., preferably between −10° C. and +80° C.

The oxidation is carried out with one equivalent of the oxidizing agent in question, for example with hydrogen peroxide in glacial acetic acid or formic acid at 0° to 60° C. or in acetone at 0° to 60° C.; with a peracid such as performic acid, peracetic acid or m-chloroperbenzoic acid at 0° to 60° C.; with sodium metaperiodate in aqueous methanol or ethanol at 15° to 30° C.; with tetrabutylammonium metaperiodate in dichloromethane or 1,2-dichloroethane at 0° to 60° C.; with N-bromosuccinimide in ethanol; with tert.butyl hypochlorite in methanol at −80° to −30° C.; with iodobenzene dichloride in aqueous pyridine at 0° to 50° C.; with chromic acid in glacial acetic acid or acetone at 0° to 40° C.; with hydrogen peroxide in aqueous methanol or in acetonitrile and in the presence of titanium (III) chloride at 10° C. to 60° C.; with potassium hydrogen peroxymonosulfate in methanol or aqueous methanol at temperatures between 0° and 60° C.; with sodium bromate in the presence of cerium (IV) nitrate in aqueous acetonitrile at 10° to 60° C.; with bromine or chlorine in a mixture of methylene chloride and water and in the presence of sodium or potassium bicarbonate at 10° to 60° C.; with hydrogen peroxide in the presence of selenium dioxide in methanol at temperatures between 10° and 60° C.; or with sulfuryl chloride in methylene chloride at −80° to −40° C. The thioether-chlorine complex primarily obtained thereby is subsequently hydrolyzed with aqueous ethanol.

The thioethers of the formula II used as starting materials are known from the literature (see U.S. Pat. No. 4,288,437).

The following are examples of specific compounds of the formula I which may be prepared by the above method:

(E)-2-[(amino)phenylmethylene]-benzo[b]thiophen-3(2H)-one-1-oxide,
(E)-2-[(methylamino)phenylmethylene]-benzo[b]thiophen-3(2H)-one-1-oxide,
(E)-2-[(dimethylamino)phenylmethylene]-benzo[b]thiophen-3(2H)-one-1-oxide,
(E)-2-[(amino)-2-fluorophenylmethylene]-benzo[b]thiophen-3(2H)-one-1-oxide,
(E)-2-[(amino)-2-chlorophenylmethylene]-benzo[b]thiophen-3(2H)-one-1-oxide,
(E)-2-[{[2-(dimethylamino)ethyl]amino}phenylmethylene]-benzo[b]thiophen-3(2H)-one-1-oxide,
(E)-2-[{2-(hydroxyethyl)amino}phenylmethylene]-benzo[b]thiophen-3(2H)-one-1-oxide,
(E)-2-[{[3-(dimethylamino)propyl]amino}phenylmethylene]-benzo[b]thiophen-3(2H)-one-1-oxide,
(E)-2-[(amino)-2-methylphenylmethylene]-benzo[b]thiophen-3(2H)-one-1-oxide,
(E)-2-[(ethylamino)phenylmethylene]-benzo[b]thiophen-3(2H)one-1-oxide,
(E)-2-[(amino)-2-bromophenylmethylene]-benzo[b]thiophen-3(2H)-one-1-oxide,
(E)-2-[(amino)-2-iodophenylmethylene]-benzo[b]thiophen-3(2H)-one-1-oxide,
(E)-2-[(amino)-4-chlorophenylmethylene]-benzo[b]thiophen-3(2H)-one-1-oxide,
(E)-2-[(amino)-4-methylphenylmethylene]-benzo[b]thiophen-3(2H)-one-1-oxide
(E)-2-[(amino)-4-fluorophenylmethylene]-benzo[b]thiophen-3(2H)one-1-oxide,
(E)-2-[(amino)phenylmethylene]-5-chlorobenzo[b]thiophen-3(2H)-one-1-oxide,
(E)-2-[(amino)phenylmethylene]-6-chlorobenzo[b]thiophen-3(2H)-one-1-oxide, (E)-2-[(amino)-2-chlorophenylmethylene]-5-chlorobenzo[b]thiophen-3(2H)-one-1-oxide,
(E)-2-[(amino)-2-fluorophenylmethylene]-5-chlorobenzo[b]thiophen-3(2H)-one-1-oxide,
(E)-2-[{[2-(dimethylamino)propyl]amino}phenylmethylene]benzo[b]thiophen-3(2H)-one-1-oxide,
(E)-2-[{[3-(dimethylamino)-2-propyl]amino}phenylmethylene]benzo[b]thiophen-3(2H)-one-1-oxide,
(E)-2-[(propylamino)phenylmethylene]-benzo[b]thiophen-3(2H)-one-1-oxide,
(E)-2-[(butylamino)phenylmethylene]-benzo[b]thiophen-3(2H)-one-1-oxide,
(E)-2-{[(2-propyl)amino]phenylmethylene}-benzo[b]thiophen-3(2H)-one-1-oxide,
(E)-2-{[(2-methylpropyl)amino]phenylmethylene}-benzo[b]-thiophen-3(2H)-one-1-oxide,
(E)-2-{[(1,1-dimethylethyl)amino]phenylmethylene}-benzo[b]thiophen-3(2H)-one-1-oxide,
(E)-2-{[(3-hydroxypropyl)amino]phenylmethylene}-benzo[b]thiophen-3(2H)-one-1-oxide,
(E)-2-[(amino)-3-methylphenylmethylene]-benzo[b]thiophen-3(2H)-one-1-oxide,
(E)-2-[(amino)-4-pyridinylmethylene]-benzo[b]thiophen-3(2H)-one-1-oxide,
(E)-2-[(amino)-3-pyridinylmethylene]-benzo[b]thiophen-3(2H)-one-1-oxide, and
(E)-2-[(amino)-2-pyridinylmethylene]-benzo[b]thiophen-3(2H)-one-1-oxide.

The following examples illustrate the present invention and will enable others skilled in the art to understand it more completely. It should be understood, however, that the invention is not limited to the particular examples given below.

EXAMPLE 1

(E)-2-[(Amino)phenylmethylene]-benzo[b]thiophen-3(2H)-one-1-oxide

A mixture of 30.0 gm (0.118 mol) of (E)-2-[(amino)-phenylmethylene]-benzo[b]thiophen-3(2H)-one, 200 ml of glacial acetic acid and 13.5 gm (0.119 mol) of an aqueous 30% hydrogen peroxide solution was heated at 50° C. for four hours while stirring, and was then allowed to stand overnight at room temperature. After the addition of 100 ml of a 10% sodium sulfite solution, the solvent was largely distilled off in vacuo, and the residue was mixed with 300 ml of water. The solid precipitated thereby was suction-filtered off and recrystallized from ethanol/ethyl acetate (1:1 v/v) using activated charcoal. 23.0 gm (72% of theory) of light yellow crystals were obtained, m.p. 246°–247° C. (decomposition).

EXAMPLE 2

(E)-2-[(Methylamino)phenylmethylene]-benzo[b]thiophen-3(2H)-one-1-oxide and (E)-2-[(Methylamino)phenylmethylene]-benzo[b]thiophen-3(2H)-one-1,1-dioxide A mixture of 6.0 gm (0.0224 mol) of (E)-2-[(methylamino)phenylmethylene]-benzo[b]thiophen-3(2H)-one, 100 ml of glacial acetic acid and 3.5 ml (0.034 mol) of an aqueous 30% hydrogen peroxide solution was heated at 50° C. for four hours while stirring and then allowed to stand overnight at room temperature. After the addition of 40 ml of a 10% sodium sulfite solution, the mixture was concentrated by evaporation in vacuo, and the residue was suspended in 200 ml of water. The solid material precipitated thereby was suction-filtered off and then broken down into its constituents by column chromatography on 300 gm of silica gel, using 1,2-dichloroethane/ethyl acetate (97:3 v/v) as the eluant. By evaporating the appropriate fractions, 2.0 gm (33% of theory) of pale yellow (E)-2-[(methylamino)-phenylmethylene]-benzo[b]thiophen-3(2H)-one-1-oxide, m.p. 205–206° C (decomposition) from ethanol), and 0.10 gm (1.5% of theory) of light yellow (E)-2-[(methylamino)phenylmethylene]-benzo[b]-thiophen-3(2H)-one-1,1-dioxide, m.p. 302°–303° C., were obtained.

EXAMPLE 3

(E)-2-[(Dimethylamino)phenylmethylene]-benzo[b]thiophen-3(2H)-one-1-oxide

Prepared analogous to Example 1 from (E)-2-[(dimethylamino)phenylmethylene]-benzo[b]thiophen-3(2H)-one and perhydrol in glacial acetic acid.
Yield: 36% of theory.
M.p. 189°–190° C.

EXAMPLE 4

(E)-2-[(Amino)-2-fluorophenylmethylene]-benzo[b]thiophen-3(2H)-one-1-oxide

Prepared analogous to Example 1 from (E)-2-[(amino)-2-fluorophenylmethylene]-benzo[b]thiophen-3(2H)-one and aqueous hydrogen peroxide in glacial acetic acid.
Yield: 50% of theory.
M.p. 220°–221° C. (ethyl acetate).

EXAMPLE 5

(E)-2-[(Amino)-2-chlorophenylmethylene]-benzo[b]thiophen-3(2H)-one-1-oxide

Prepared analogous to Example 1 from (E)-2-[(amino)-2-chlorophenylmethylene]-benzo[b]thiophen-3(2H)-one and aqueous hydrogen peroxide in glacial acetic acid.
Yield: 54% of theory.
M.p. 255°–256° C. (decomposition). (Methanol:ethyl acetate 1:1 v/v).

EXAMPLE 6

(E)-2-[(Amino)-2-bromophenylmethylene]-benzo[b]thiophen-3(2H)-one-1-oxide and (E)-2-[(Amino)-2-bromophenylmethylene]-benzo[b]thiophen-3(2H)-one-1,1-dioxide Prepared analogous to Example 2 from (E)-2-[(amino)-2-bromophenylmethylene]-benzo[b]thiophen-3(2H)-one and aqueous hydrogen peroxide in glacial acetic acid.
Yield: 32% of theory of pale yellow (E)-2-[(amino)-2-bromophenylmethylene]-benzo[b]thiophen-3(2H)-one-1-oxide, m.p. 243°–244° C. (decomposition) (methanol:ethyl acetate 1:1 v/v), and 18% of theory of light yellow (E)-2-[(amino)-2-bromophenylmethylene]-benzo[b]thiophen-3(2H)-one-1,1-dioxide, m.p. 262–263° C.

EXAMPLE 7

(E)-2-[(Amino)-2-methylphenylmethylene]-benzo[b]thiophen-3(2H)-one-1-oxide

Prepared analogous to Example 1 from (E)-2-[(amino)-2-methylphenylmethylene]-benzo[b]thiophen-3(2H)-one and aqueous hydrogen peroxide in glacial acetic acid.

Yield: 86% of theory.
M.p. 231°–232° C. (decomposition) (ethanol).

EXAMPLE 8

(E)-2-[(Amino)-4-fluorophenylmethylene]-benzo[b]thiophen-3(2H)-one-1-oxide

Prepared analogous to Example 1 from (E)-2-[(amino)-4-fluorophenylmethylene]-benzo[b]thiophen-3(2H)-one and perhydrol in glacial acetic acid.
Yield: 75% of theory.
M.p. 235°–236° C. (glacial acetic acid/ethanol 1:4 v/v).

EXAMPLE 9

(E)-2-{[(2-Hydroxyethyl)amino]phenylmethylene}-benzo[b]thiophen-3(2H)-one-1-oxide Prepared analogous to Example 1 from (E)-2-{[(2-hydroxy ethyl)amino]phenylmethylene}-benzo[b]thiophen-3(2H)-one and perhydrol in glacial acetic acid.
Yield: 64% of theory.
M.p.: 178°–179° C. (ethanol).

EXAMPLE 10

(E)-2-[(Amino)phenylmethylene]-5-chlorobenzo[b]thiophen-3(2H)-one-1-oxide hemihydrate and (E)-2-[(Amino)phenylmethylene]-5-chlorobenzo[b]thiophen-3(2H)-one-1,1-dioxide Prepared analogous to Example 2 from (E)-2-[(amino)phenylmethylene]-5-chlorobenzo[b]thiophen-3(2H)-one and aqueous hydrogen peroxide in glacial acetic acid.
Yield: 53% of theory of (E)-2-[(amino)phenylmethylene]-5-chlorobenzo[b]thiophen-3(2H)-one-1-oxide hemihydrate, m.p.: 251°–252° C. (ethyl acetate), and 18% of theory of (E)-2-[(amino)phenyl methylene]-5-chlorobenzo[b]thiophen-3(2H)-one-1,1-dioxide, m.p. 263°–264° C.

EXAMPLE 11

(E)-2-[{[2-(Dimethylamino)ethyl]amino}phenylmethylene]-benzo[b]thiophen-3(2H)-one-1-oxide Prepared analogous to Example 1 from (E)-2-[{[2-(dimethylamino)ethyl]amino}phenylmethylene]-benzo[b]-thiophen-3(2H)-one and perhydrol in glacial acetic acid.
Yield: 29% of theory.
M.p.: 174°–176° C. (ethyl acetate).

EXAMPLE 12

(E)-2-[(Ethylamino)phenylmethylene]-benzo[b]thiophen-3(2H)-one-1-oxide

Prepared analogous to Example 1 from (E)-2-[(ethylamino)phenylmethylene]-benzo[b]thiophen-3(2H)-one and aqueous hydrogen peroxide in glacial acetic acid.
Yield: 11% of theory.
M.p.: 183°–185° C.

EXAMPLE 13

(E)-2-[(Amino)-2-chlorophenylmethylene]-5-chlorobenzo[b]- thiophen-3(2H)-one-1-oxide 2.5 gm (0.0078 mol) of (E)-2-[(amino)-2-chlorophenylmethylene]-5-chlorobenzo[b]thiophen-3(2H)-one were dissolved in 150 ml of methanol, and then mixed with a solution of 6.15 gm (0.01 mol) of "oxone monopersulfate" (KHSO$_5$×KHSO$_4$×K$_2$SO$_4$; supplied by Ventron GmbH) in 50 ml of water, and the mixture was heated at 50° C. for one hour while stirring. After cooling, the reaction mixture was stirred into 500 ml of ice water and then extracted exhaustively with dichloromethane. The combined extracts were washed with water and dried over sodium sulfate, and the solvent was removed in vacuo. The crude product thus obtained was ourified by coulmn chromatography on 200 gm of silicagel, using dichloromethane/ethyl acetate (97:3 v/v) as the eluant. By evaporation of the appropriate fractions, light yellow crystals were obtained, m.p. 248° C. (decomposition; ethanol).
Yield: 1.5 gm (57% of theory).

EXAMPLE 14

(E)-2-[(Amino)phenylmethylene]-5-methylbenzo[b]thiophen-3(2H)-one-1-oxide monohydrate Prepared analogous to Example 1 from (E)-2-[(amino)phenylmethylene]-5-methylbenzo[b]thiophen-3(2H)-one and aqueous hydrogen peroxide in glacial acetic acid.
Yield: 45% of theory.
M.p.: 233°–235° C. (ethyl acetate).

EXAMPLE 15

(E)-2-[(Amino)phenylmethylene]-benzo[b]thiophen-3(2H)-one-1-oxide

Prepared analogous to Example 13 from (E)-2-[(amino)phenylmethylene]-benzo[b]thiophen-3(2H)-one and "oxone monopersulfate", but using ethanol instead of methanol.
Yield: 66% of theory.
M.p.: 246°–247° C. (ethanol).

EXAMPLE 16

(E)-2-[(Amino)phenylmethylene]-benzo[b]thiophen-3(2H)-one-1oxide

A solution of 2.246 gm (0.0105 mol) of sodium metaperiodate in 10 ml of water was added to a solution of 2.53 gm (0.01 mol) of (E)-2-[(amino)phenylmethylene]-benzo[b]-thiophen-3(2H)-one in 150 ml of methanol, and the mixture was stirred at room temperature for 15 hours. The sodium iodate precipitated thereby was removed by filtration, and the filtrate was diluted with 300 ml of water and extracted exhaustively with dichloromethane. The combined extracts were washed once with water, dried over sodium sulfate and concentrated by evaporation in vacuo. The residue was recrystallized from ethanol/ethyl acetate using activated charcoal, and yielded 2.28 gm (85% of theory) of pale yellow crystals, m.p. 246°–247° C. (decomposition).

EXAMPLE 17

(E)-2-[(Amino)phenylmethylene]-benzo[b]thiophen-3(2H)-one-1-oxide 1.18 gm (4.66 mmols) of (E)-2-[(amino)phenylmethylene]-benzo[b]thiophen-3(2H)-one were dissolved in 50 ml of methanol and mixed with 0.9 gm (4.94 mmols) of N-bromo-succinimide. The mixture was stirred at room temperature for 15 hours, diluted with 500 ml of hot water (60° C.), and decanted off the residue which crystallized. After recrystallization from ethanol, 0.83 gm (66% of theory) of pale yellow crystals were obtained, m.p. 245°–247° C. (decomposition).

EXAMPLE 18

(E)-2-[(Amino)-4-fluorophenylmethylene]-benzo[b]thiophen-3(2H)-one-1-oxide 2.61 gm (9.61 mmols) of (E)-2-[(amino)-4-fluorophenylmethylene]-benzo[b]thiophen-3(2H)-one were dissolved in 50 ml of dichloromethane, the solution was cooled to $-70°$ C, and then a solution of 1.5 gm (11.1 mmols) of sulfuryl chloride in 5 ml of dichloroethane was added dropwise thereto. After 15 hours, 20 ml of 95% ethanol were added, and the reaction mixture was brought to room temperature by removal of the cooling bath. It was then neutralized with aqueous sodium carbonate, the dichloromethane phase was dried with sodium sulfate, the solvent was evaporated in vacuo, and the residue was recrystallized from glacial acetic acid/ethanol (1:4 v/v).

Yield: 2.24 gm (81% of theory).
M.p. 235°–236° C.

EXAMPLE 19

(E)-2-[(Amino)phenylmethylene]-benzo[b]thiophen-3(2H)-one-1-oxide A mixture of 0.51 gm (2 mmols) of (E)-2-[(amino)-phenyl-methylene]-benzo[b]thiophen-3(2H)-one, 378 mg (2.5 mmols) of sodium bromate and 28 mg (0.051 mmols) of ammonium cerium (IV) nitrate in 10 ml of aqueous acetonitrile (7:3 v/v) was stirred vigorously at room temperature for 5 hours. The mixture was diluted with 200 ml of water, and the product which crystallized out was suction-filtered off. After recrystallization from ethanol/ethyl acetate (1:1 v/v) using activated charcoal, 0.49 gm (91% of theory) of pale yellow crystals, m.p. 246°–247° C. (decomposition), were obtained.

EXAMPLE 20

(E)-2-[(Amino)phenylmethylene]-benzo[b]thiophen-3(2H)-one-1-oxide

A 250 ml three-necked round bottom flask was charged with 30 ml of dichloromethane, 2.53 gm (10 mmols) of (E)-2-(amino)phenylmethylene]-benzo[b]thiophen-3(2H)-one and 20 ml of a 10% potassium bicarbonate solution. A solution of 1.6 gm (10 mmols) of bromine in 20 ml of dichloromethane was added dropwise thereto, while stirring, over a period of one hour, and the resulting mixture was then maintained at room temperature for 4 hours. After this time, the reddish-brown bromine color had disappeared. The lower organic phase was separated, the aqueous phase was extracted twice more with 50 ml of methylene chloride, and the organic extracts were combined and then dried over sodium sulfate. The residue which remained after the solvent had been evaporated was recrystallized from ethanol.

Yield: 2.56 gm (95% of theory).
M.p. 246°–247° C. (decomposition).

If the equivalent quantity of chlorine is used instead of bromine as the oxidizing agent, under otherwise identical conditions, the reaction ends after 20 minutes.

Yield: 88% of theory.
M.p.: 245°–247° C. (decomposition; ethanol).

EXAMPLE 21

(E)-2-[(Amino)phenylmethylene]-benzo[b]thiophen-3(2H)-one-1-oxide

A solution of 1.1 ml (10.8 mmols) of 30% hydrogen peroxide and 1.1 gm (10 mmols) of selenium dioxide in 5 ml of water was added dropwise, while stirring, to a solution of 2.53 gm (10 mmols) of (E)-2-[(amino)phenylmethylene]-benzo[b]thiophen-3(2H)-one in 20 ml of methanol. The reaction temperature was not allowed to exceed $+25°$ C. After 20 minutes, the reaction mixture was diluted with 100 ml of water, the reaction product was separated by suction filtering and recrystallized from ethanol/ethyl acetate (1:1 v/v) using activated charcoal.

Yield: 2.32 gm (86% of theory).
M.p.: 246°–247° C. (decomposition).

EXAMPLE 22

(E)-2-[(Amino)phenylmethylene]-benzo[b]thiophen-3(2H)-one-1-oxide 7.6 gm (0.003 mol) of (E)-2-[(amino)phenylmethylene]-benzo[b]thiophen-3(2H)-one and 13.75 gm (0.03 mol) of tetrabutylammonium periodate (prepared from tetrabutylammonium hydrogen sulfate and sodium metaperiodate in water) in 50 ml of dichloromethane were refluxed for about 2 hours. After the end of the reaction, which was monitored by thin-layer chromatography, the mixture was allowed to cool and was then filtered through a column of silicagel (200 gm), finally using dichloromethane/ethyl acetate (97:3 v/v) as the eluant. By evaporating the appropriate fractions and subsequently recrystallizing the residue from ethanol, 5.8 gm (72% of theory) of pale yellow crystals, m.p. 246°–247° C. (decomposition), were obtained.

EXAMPLE 23

(E)-2-[(Ethylamino)phenylmethylene]-benzo[b]thiophen-3(2H)-one-1-oxide 3.2 ml (0.031 mol) of aqueous 30% hydrogen peroxide, dissolved in 15 ml of methanol, was added dropwise, while vigorously stirring, to a solution of 1.97 gm (0.007 mol) of (E)-2-[(ethylamino)phenylmethylene]-benzo[b]thiophen-3(2H)-one and 10 ml of an aqueous 16% solution of titanium (III) chloride in 100 ml of methanol and 20 ml of water. The course of the reaction was monitored by thin-layer chromatography. After the reaction had ended, the mixture was diluted with 300 ml of water, and the precipitate thus obtained was suction-filtered off and then recrystallized twice from ethanol. 1.75 gm (84% of theory) of pale yellow crystals, m.p. 183°–185° C., were obtained.

EXAMPLE 24

(E)-2-[(Amino)phenylmethylene]-benzo[b]thiophen-3(2H)-one-1-oxide

A solution of 107.0 gm (0.500 mol) of sodium metaperiodate in 800 ml of water was added in portions to a suspension of 127.0 gm (0.501 mol) of (E)-2-[(amino)-phenylmethylene]benzob-[b]thiophen-3(2H)-one in 4 liters of ethanol, and the mixture was stirred at room temperature for 12 hours. Then, another 54.0 gm (0.252 mol) of sodium metaperiodate dissolved in 500 ml of water were added, together with 2 liters of ethanol, and the resulting mixture was stirred for 8 hours at room temperature.

Then, the mixture was stirred into 6 liters of water, and the product precipitated thereby was suction-filtered off. The filter cake was washed three times with 200 ml of warm water (40° C.) and once with 200 ml of cold methanol, and was then recrystallized from the smallest possible quantity of dimethylformamide. The product thus obtained was dissolved in 200 ml of a mixture of methanol and chloroform (1:1 v/v), treated with 3 gm of animal charcoal and filtered while hot. The filtrate was evaporated to a quarter of its original volume and kept at room temperature overnight. The precipitate was then suction-filtered off and washed again with diethyl ether and dried at 110° C. in vacuo. 98.0 gm (73% of theory) of pale yellow crystals, m.p. 246–247 (decomposition) were obtained.

EXAMPLE 25

(E)-2-[(Amino)-2-pyridinylmethylene]-benzo[b]thiophen-3(2H)-one-1-oxide

Prepared analogous to Example 24 from (E)-2-[(amino)-2-pyridinylmethylene]-benzo[b]thiophen-3(2H)-one and sodium metaperiodate.

Yield: 33% of theory.

M.p. 186°–187° C. (ethyl acetate).

EXAMPLE 26

(E)-2-[(Amino)-4-pyridinylmethylene]-benzo[b]thiophen-3(2H)-one-1-oxide

Prepared analogous to Example 24 from (E)-2-[(amino)-4-pyridinylmethylene]-benzo[b]thiophen-3(2H)-one and sodium metaperiodate.

Yield: 80% of theory.

M.p. 259°–260° C. (ethyl acetate).

The compounds of the present invention, that is, those embraced by formula I above, have useful pharmacodynamic properties. More particularly, they exhibit CNS-activity, especially anticonvulsant activity in warm-blooded animals such as mice and rats, and, unlike known anticonvulsants of similar structure, do not produce a strong yellow coloration of the fatty and cartilaginous tissue.

The anticonvulsant properties of the compounds of this invention were ascertained by the standard test methods described below, and the results of these tests for a few representative species of the genus are shown in the tables, where A = (E)-2-[(amino)phenylmethylene]-benzo[b]thiophen-3(2H)-one-1-oxide, B = (E)-2-[(amino)-2-chlorophenylmethylene]-benzo[b]thiophen-3(2H)-one-1-oxide, and C = (E)-2-[(ethylamino)phenylmethylene]-benzo[b]thiophen-3(2H)-one-1-oxide.

1. Anticonvulsant activity in mice

The anticonvulsant activity was tested by measuring the inhibition of tonic extensor spasm in the back legs of male mice subjected to maximum electric shock.

Method:

The test animals used were male SPF mice (Chbb:NMRI) weighing from 20–26 gm which had access to standard food and drinking water up to one hour before the oral administration of the test substance.

The test was carried out using the method described by Swinyard, Brown and Goodman (J. Pharmacol. Exp. Ther. 106, 319, [1952]). The electric shock apparatus was constructed in accordance with the specifications provided by Woodbury and Davenport (Arch. Int. Pharmacodyn. 92, 97, [1952]). The electrical stimuli were administered to the animals' temples above their eyes, through steel ball electrodes covered with chamois and moistened with 0.9% NaCl solution. The stimuli were administered using alternating current, 50 Hz and 50 mA, with a duration of 0.2 sec. In all the control animals, clonic and then tonic extension spasms of the extremities occurred; in the animals protected by the anticonvulsant agents, the tonic extension spasm did not occur.

The substance to be tested was suspended in 1% tylose mucilage and administered orally in a volume of 0.1 ml/10 gm body weight of the mice, each dosage being administered to 10 mice. The animals were given the shocks 30, 150 and 300 minutes after the administration of the test substance, and the $ED_{50}$ values were determined graphically or by using the method of Litchfield and Wilcoxon (J. Pharmacol. Exp. Ther. 96, 99, [1949]) from the dosage which protects 50% of the animals from the tonic extension spasm of the rear extremities.

Results:

TABLE 1

| Compound | $ED_{50}$ mg/kg p.o. | | |
|---|---|---|---|
| | 30 | 150 | 300 minutes |
| A | 12.5 | 35 | 88 |
| B | 8.1 | 7.4 | 8.3 |
| C | 17.1 | 61.0 | 93.9 |

2. Anticonvulsant activity in rats

The anticonvulsant activity was tested by measuring the inhibition of tonic extensor spasms in the back legs of male rats subjected to maximum electric shock.

Method:

The test animals used were male SPF rats (Chbb:THOM) weighing from 100–120 gm which had access to standard food and drinking water up to one hour before the oral administration of the test substance.

The test was carried out using the method described by Swinyard, Brown and Goodman (J. Pharmacol. Exp. Ther. 106, 319, [1952]). The electric shock apparatus was constructed in accordance with the specifications provided by Woodbury and Davenport (Arch. Int. Pharmacodyn. 92, 97 [1952]). The electrical stimuli were applied to the temples above the eyes, using moistened steel ball electrodes. The parameters of the stimuli were as follows: alternating current 50 Hz, 50 mA, duration of stimulus 0.2 sec. In all the control animals, clonic and then tonic extension spasm of the extremities occurred; the latter can be prevented by means of effective anticonvulsant agents.

The substance to be tested was suspended in 2% tylose mucilage and administered orally, in a volume of 1 ml/100 gm body weight of the rat, in dosages of 1.56, 3.125, 6.25 and 12.5 mg/kg, each dose being administered to 6 rats. One hour later, the animals were subjected to electric shock and the $ED_{50}$ was calculated as the dosage which protected 50% of the animals against tonic extension spasms in the rear extremities, with confidence limits for a 5% probability of error.

Results:

TABLE 2

| Maximum electric spasm in rats, compound A. | | | |
|---|---|---|---|
| Dosage mg/kg p.o. | N | animals protected | % protected |
| 1.56 | 6 | 0 | 0 |
| 3.125 | 6 | 4 | 67 |
| 6.25 | 6 | 5 | 83 |
| 12.5 | 6 | 6 | 100 |

$ED_{50}$ (confidence limits, $p \leq 0.05$) = 3.25 (2.01–5.27) mg/kg p.o.

3. Tolerance of compound in mice and rats

The new compound A was found to be well tolerated, as shown in Table 3 below, which gives a guide to the toxicity of the substance in mice after oral administration.

TABLE 3

| Approximate acute toxicity in mice, compound A, p.o. | | |
|---|---|---|
| Dosage mg/kg p.o. | N | Number of animals which died in 14 days |
| 500 | 10 | 0 |
| 1000 | 16 | 1 |
| 1410 | 10 | 0 |
| 2000 | 10 | 2 |
| 4000 | 10 | 1 |

The $LD_{50}$ for the mouse is therefore $>4000$ mg/kg p.o.

In rats with a body weight of 200 gm compound A only had toxic effects in very large dosages (Table 4).

TABLE 4

| Acute toxicity in the rat, compound A, p.o. | | | |
|---|---|---|---|
| Dosage mg/kg | N | Animals which died in 14 days | % |
| 1000 | 10 | 0 | 0 |
| 2000 | 10 | 4 | 40 |
| 4000 | 10 | 7 | 70 |

$LD_{50}$ (confidence limits, $p \leq 0.05$) = 2600 (1756–3848) mg/kg p.o.

Thus, the average toxic dose in the rat is 800 times the average therapeutic dose.

Furthermore, in the pharmacological screening of the substances tested, no toxic side effects were observed even at the highest doses tested (up to 200 mg/kg p.o.).

4. Tests for yellow coloration of fatty and cartilaginous tissue in the rat

The known compound (E)-2-[(amino)phenylmethylene]-benzo[b]thiophen-3(2H)-one = E (cf. German Offenlegungsschrift No. 2,931,010 or U.S. Pat. No. 4,288,437) has an undesirable side effect, namely a strong yellow coloration which is released into fatty and cartilaginous tissue. If used in long-term treatments, such as the treatment of spastics and epileptics, the yellow coloration caused by this compound is very likely to penetrate into skin tissue and therefore become visible to others, which is a significant limitation for its practical application.

The yellow coloration of fatty and cartilaginous tissue following the oral administration of 50 and 400 mg/kg of compound E and compound A once a day over a period of 5½ weeks was investigated.

Method:

The compounds were homogeneously suspended in 1.5% tylose by several hours' stirring.

The compounds were administered through an esophageal tube. The volume administered was about 1.4 ml. 9 to 11 male rats [of the Chbb:THOM (SPF) strain] with a body weight of 263±10 gm were used for each dose.

At different times, animals were taken from the four treated groups and one control group and the kidney fat and sternum were removed after the animal had been bled from the abdominal aorta.

Results:

Only when 400 mg/kg of compound E were administered was it possible to observe, from the 17th day p.a., a yellow coloration of the kidney fat and sternum, which was slight at first but became marked later.

TABLE 5

| | Number of animals with yellow kidney fat and sternum (Number of animals dissected shown in brackets) | | | |
|---|---|---|---|---|
| Duration of treatment in days | Compound E | | Compound A | |
| | 50 (mg/kg) | 400 (mg/kg) | 50 (mg/kg) | 400 (mg/kg) |
| 2 | — | 0 (1) | — | 0 (1) |
| 4 | — | 0 (1) | — | 0 (1) |
| 9 | — | 0 (1) | — | 0 (1) |
| 17 | 0 (1) | 1 (1) very slight | 0 (1) | 0 (1) |
| 36 | 0 (1) | 1 (1) marked | 0 (1) | 0 (1) |
| 38 | 0 (1) | 1 (1) marked | 0 (1) | 0 (1) |
| 39 | 0 (6) | 5 (5) marked | 0 (6) | 0 (2) |

The novel compounds of the formula I according to the present invention are thus particularly suitable for the long-term treatment of spastic conditions and epilepsy.

For pharmaceutical purposes the compounds of the present invention are administered to warm-blooded animals perorally or parenterally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups and the like. An effective amount of the compounds according to the present invention is from 0.5 to 5.0 mgm/kg body weight, preferably 1 to 3 mgm/kg body weight, 2 to 4 times daily.

The following examples illustrate a few pharmaceutical compositions comprising a compound of the present invention as an active ingredient and represent the best modes contemplated of using the invention. The parts are parts by weight unless otherwise specified.

EXAMPLE 27

Tablets

The tablet composition is compounded from the following ingredients:

| | |
|---|---|
| (E)-2-[(Amino)phenylmethylene]-benzo-[b]thiophen-3(2H)—one-1-oxide | 50 parts |
| Lactose | 148 parts |
| Potato Starch | 60 parts |
| Magnesium stearate | 2 parts |
| Total | 260 parts |

Preparation:

The active ingredient and the lactose are stirred into an aqueous 10% potato starch solution, and the mixture is granulated through a screen with a mesh size of 1.5 mm; the granulate is dried and passed through the same screen again, then the magnesium stearate is added and the mixture is compressed into 260 mgm-tablets. Each tablet contains 50 mg of the active ingredient.

EXAMPLE 28

Coated Tablets

The tablets prepared in accordance with Example 31 are coated with a thin shell consisting essentially of a mixture of sugar and talcum, and the coated tablets are polished with beeswax.

Any one of the other compounds embraced by formula I or a non-toxic, pharmacologically acceptable acid addition salt thereof may be substituted for the particular active ingredient in Examples 27 and 28. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

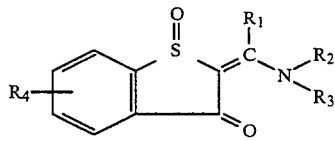

wherein $R_1$ is phenyl, halo-substituted phenyl, methyl-substituted phenyl, halo- and methyl-substituted phenyl or pyridinyl;

$R_2$ is hydrogen, straight or branched alkyl of 1 to 4 carbon atoms, 2- or 3-hydroxy-(alkyl of 2 to 3 carbon atoms) or 2- or 3-dimethylamino-(alkyl of 2 to 3 carbon atoms);

$R_3$ is hydrogen or alkyl of 1 to 3 carbon atoms; and $R_4$ is hydrogen, chlorine or methyl.

2. A compound of claim 1, where $R_1$ is phenyl, methyl-phenyl, fluoro-phenyl, chloro-phenyl or bromo-phenyl;

$R_2$ is hydrogen, alkyl of 1 to 3 carbon atoms or 2-hydroxy-ethyl;

$R_3$ is hydrogen or methyl; and $R_4$ is hydrogen, chlorine or methyl.

3. A compound of claim 1, where $R_1$ is phenyl, 2-chloro-phenyl or 2-bromo-phenyl, and $R_2$, $R_3$ and $R_4$ are each hydrogen.

4. The compound of claim 1 which is (E)-2-[(amino)-phenylmethylene]-benzo[b]thiophen-3(2H)-one-1-oxide.

5. The compound of claim 1 which is (E)-2-[(amino)-2-chlorophenylmethylene]-benzo[b]thiophen-3(2H)-one-1-oxide.

6. The compound of claim 1 which is (E)-2-[(ethylamino)-phenylmethylene]-benzo[b]thiophen-3(2H)-one-1-oxide.

7. An anticonvulsant pharmaceutical composition consisting essentially of an inert pharmaceutical carrier and an effective anticonvulsant amount of a compound of claim 1.

8. The method of preventing or relieving convulsions in a warm-blooded animal in need thereof, which comprises perorally or parenterally administering to said animal an effective anticonvulsant amount of a compound of claim 1.

* * * * *

UNITED STATES PATENT AND TRADEMARK OFFICE
CERTIFICATE OF CORRECTION

PATENT NO. : 4,536,402

DATED : Aug. 20, 1985

INVENTOR(S) : WOLFHARD ENGEL ET AL.

It is certified that error appears in the above-identified patent and that said Letters Patent is hereby corrected as shown below:

Column 6, line 8: "ourified" should read -- purified --.

Column 6, line 39: "loxide" should read -- 1-oxide --.

Column 8, line 56: "benzob-" should read -- benzo --.

Signed and Sealed this

Third Day of June 1986

[SEAL]

Attest:

DONALD J. QUIGG

Attesting Officer

Commissioner of Patents and Trademarks